United States Patent [19]
Ishibashi et al.

[11] Patent Number: 5,804,174
[45] Date of Patent: Sep. 8, 1998

[54] DEODORIZER

[75] Inventors: Sadami Ishibashi, Sakado; Tadao Hamaya, Ageo; Tadashi Imai; Masao Iijima, both of Tokyo, all of Japan

[73] Assignees: Ricom Corporation; Zeria Pharmaceuticals; Mitsui & Company Ltd., all of Tokyo, Japan

[21] Appl. No.: 777,603

[22] Filed: Dec. 31, 1996

Related U.S. Application Data

[62] Division of Ser. No. 107,333, Aug. 16, 1993, Pat. No. 5,639,470, which is a continuation of Ser. No. 469,330, Jan. 24, 1990, abandoned.

[30] Foreign Application Priority Data

Jan. 25, 1989 [JP] Japan ...................................... 1-14055
Jul. 7, 1989 [JP] Japan ..................................... 1-176842

[51] Int. Cl.⁶ ...................................................... A61L 9/01
[52] U.S. Cl. ..................... 424/76.9; 424/195.1; 424/439; 426/321
[58] Field of Search ................................... 424/439, 76.9, 424/195.1; 426/321, 335

[56] References Cited

U.S. PATENT DOCUMENTS

| | | |
|---|---|---|
| 4,370,351 | 1/1983 | Harper . |
| 4,472,046 | 9/1984 | Bliah . |
| 4,512,983 | 4/1985 | Shino et al. . |

FOREIGN PATENT DOCUMENTS

| | | |
|---|---|---|
| 3524473 | 1/1987 | Germany . |
| 63-3864 | 1/1988 | Japan . |
| 3-119974 | 5/1991 | Japan . |
| 5-38358 | 2/1993 | Japan . |
| 1477882 | 6/1977 | United Kingdom . |

OTHER PUBLICATIONS

The Patent Office of Japanese Government "Patent Abstracts of Japan," vol. 13, No. 384 (C–629) (3732), p. 36 C 629 JP–A–01 132 356(A), Aug. 24, 1989.

*Primary Examiner*—S. Mark Clardy
*Assistant Examiner*—Robert H. Harrison
*Attorney, Agent, or Firm*—Seed & Berry LLP

[57] ABSTRACT

A deodorizer comprises a hydrophilic solvent extract of fruit-bodies of champignon mushroom or powder of the extract as an effective component. The extract of champignon mushroom used as an effective component can be prepared by a method which comprises the step of immersing the mushroom in a hydrophilic solvent at a temperature ranging from 60° to 1000° C. for 15 minutes to 2 hours to perform extraction. The extract can further be treated to obtain the effective components in the form of powder. The extract and the powder thereof can be used as an effective component of a deodorizer capable of oral intake, which serves as a deodorizer for preventing bad smell of environment or an agent for preventing foul breath, which can also be used in foods for eating or drinking to prevent giving out of bad smell emitted from cookings such as those containing garlic and leek as well as cooked fish, which can prevents giving out of bad smell after taking such cookings, and which can be involved in metabolism to thus suppress the giving out of bad smell from urine and feces discharged after eating and drinking such foods.

2 Claims, No Drawings

DEODORIZER

CROSS-REFERENCE TO RELATED APPLICATIONS

This application is a division of U.S. patent application Ser. No. 08/107,333, filed Aug. 16, 1993, U.S. Pat. No. 5,639,470 which is a continuation of U.S. patent application Ser. No. 07/469,330, filed Jan. 24, 1990, now abandoned.

BACKGROUND OF THE INVENTION

1. Field of the Invention

The present invention relates to a deodorizer which is safe for human bodies, as well as foods, feeds, buccal compositions and aerosol compositions containing such a deodorizer.

2. Description of the Prior Art

As recent advancement in quality of life proceeds, the problem of bad smell originated from individual bodies such as foul breath and body smell has become a matter of great concern. Such a problem has greatly affected even personal relations. Thus, there have been proposed a variety of mouth wash liquids for removing or preventing foul breath. However, most of these mouth wash liquids often contain ingredients undesirable for internal use and the use thereof is restricted to the deodorization of mouth.

On the other hand, there have already been proposed those which make use of components present in foods, while taking safety thereof into consideration. For instance, the following substances are known to be effective as deodorizers: green tea extract (see Japanese Patent Un-examined Publication (hereunder referred to as "J.P. KOKAI") No. Sho 60-185558); red beetroot, cacao beans, coffee beans and parsley extracts (J.P. KOKAI No. Sho 60-207664); perilla extract (J.P. KOKAI No. Sho 60-214726); persimmon extract (J.P. KOKAI No. Sho 61-87562); butterburr plant extract (J.P. KOKAI No. Sho 61-206448); laver (J.P. KOKAI No. Sho 62-152463); and finely ground material of bracket fungus of the genus Fomes (J.P. KOKAI No. Sho 62-181048).

As other deodorizers effectively used in the field of foods, there have simply been proposed dimethylaminosulfonate, glucosamine (J.P. KOKAI No. Sho 48-23946), cyclodextrin (J.P. KOKAI No. Sho 55-122700), organic acids such as l-ascorbic acid, benzoic acid, gluconic acid, folic acid and nicotinic acid and salts thereof (J.P. KOKAI No. Sho 60-136506).

However, all of these compounds can never prevent giving out of bad smell, discharged from the inside of the body after any foods are internally taken, such as bad smell of a belch eructed after eating a dumpling stuffed with minced pork, bad smell of urine discharged after drinking alcoholic drinks and bad smell of feces discharged after taking meat.

SUMMARY OF THE INVENTION

Accordingly, an object of the present invention is to provide a deodorizer capable of oral intake, which prevents bad smell of environment or foul breath, which can also be used in foods or drinking to prevent giving out of bad smell emitted from cookings such as those containing garlic and leek as well as cooked fish, which can prevent giving out of bad smell after taking such cookings, and which can be involved in metabolism to thus suppress the giving out of bad smell from urine and feces discharged after eating and drinking such foods giving out bad smell.

A further object of the present invention is to provide foods, feeds, buccal composition and aerosol compositions containing the deodorizer.

The foregoing objects can effectively be achieved by providing a deodorizer comprising a hydrophilic solvent extract of fruit-bodies of champignon mushroom (technical name: *Agaricus Bisporus*) or powder of the extract as an effective component.

According to another aspect of the present invention, there is provided a food, a feed, a buccal composition or an aerosol composition containing the hydrophilic solvent extract of champignon mushroom or powder of the extract.

DETAILED EXPLANATION OF THE INVENTION

The present invention will hereinafter be described in more detail.

There have already been known deodorizers obtained from Hymenomycetes (see J.P. KOKAI No. Sho 62-181048), but Sho 62-181048 principally aims at the use of the fruit-body per se of mushrooms which grow on wood such as bracket fungus of the genus Fomes as an adsorbent but does not aim at the use of extracts derived from soft edible mushrooms which are designed to be suitable for oral intake.

The effective components of the fruit-bodies of champignon mushroom varies depending on the degree of mature and portions from which the components are extracted. To obtain the extract of the present invention, it is preferred to properly determine the time for harvesting the fruit-bodies of champignon mushroom or alternatively to change the method for extracting depending on the portions thereof to be extracted.

In addition, the mycelium in compost also includes the effective components, but products favorable for oral intake cannot be obtained from the mycelium for the reasons, for instance, that the efficiency of extract thereof is very low and that a large amount of contaminants originated from the compost are mingled in the products during extraction processes.

The fruit-body of champignon mushroom which is usually used for food is one in the course of growth and whose cap has not yet completely grown (closed cap). In the present invention, it is likewise preferred to use the fruit-body harvested at this time from the viewpoint of coloring. Portions of the fruit-body to be used are not restricted to specific ones, but the use of cap portion thereof is particularly preferred in the invention.

The extraction of effective components from the fruit-body of champignon mushroom is preferably carried out by cutting, into thin pieces, fresh one which has not yet caused browning or those frozen or freeze-dried when they are still fresh and introducing the sliced pieces of the fruit-body into a hot solvent for extraction immediately after cutting. The cut mushroom immediately causes browning due to the action of phenoloxidase which in turn leads to the decomposition of the effective components. It is also effective for preventing such browning to treat the fruit-body by immersing in or spraying with an organic or inorganic acid solution having a concentration of not less than 0.1%.

On the other hand, the mature mushroom having an open cap can also be employed in the invention and it can be immersed in cold water for 10 minutes to one hour to thus extract effective components from dark purple spores and gills of the fruit-body. The extract is initially colored deep purple and causes aggregation or precipitation if it is allowed to stand at a cold place over night to give a clear liquid. This liquid is inferior in thermal stability and, therefore, it is preferred to store and use the same after freezing and drying to obtain the desired effective components in the form of powder.

As solvents for extraction, there may be used, for instance, hydrophilic solvents such as methanol, ethanol, isopropyl alcohol, acetone and mixture thereof in addition to water. However, water and/or ethanol are particularly preferred because they do not exert any adverse effect on foods containing them. The weight ratio of water to ethanol preferably ranges from 20/80 to 80/20 when a mixture of water and ethanol is employed. The solvent for extraction is in general added to the raw material in an amount ranging from 2 to 10 times (by weight) per unit weight of the latter. The extraction is preferably performed at 60° to 100° C. for 15 minutes to 2 hours, more preferably at 80° to 95° C. for 30 minutes to one hour.

The extraction is preferably carried out using a mixture of water and an alcohol or acetone rather than using an alcohol or acetone separately. In this case, the weight ratio of water to an alcohol or acetone preferably ranges from 20/80 to 80/20.

Moreover, an organic acid or a sugar component may be added to the solvent for extraction whereby the extraction of the effective components can be performed efficiently.

Preferred examples of such organic acids include citric acid, malic acid, acetic acid and ascorbic acid. The amount of these organic acids ranges from 0.05 to 2% by weight on the basis of the total weight of the solvent used whereby a pH value of the extraction solvent is adjusted to 3.0 to 5.0.

Examples of the sugar components used in the invention are fructose, glucose, sucrose and maltose. The amount thereof added to the extraction solvent desirably ranges from 0.5 to 5% by weight on the basis of the total weight of the solvent. In this case, the effective components present in the cell wall of the fruit-body can effectively be extracted by the action of a high osmotic pressure due to the presence of such sugar components.

Alternatively, it is also possible to perform such extraction after adding 0.01 to 0.1% by weight of cellulase or amylase to water and carrying out a reaction at 25° to 40° C. for 2 to 24 hours to decompose the cell wall or proteins. Furthermore, the mushroom is first frozen and then thawed to destruct tissues (cell wall) whereby the effective components can efficiently be extracted.

In the present invention, the fruit-body of the mushroom can previously be lyophilized and then extracted.

The reason why the product of the present invention can prevent giving out of bad smell and can show deodorization effect through metabolism has not yet clearly elucidated, but it is thought that polyhydric phenols, amino acid type compounds, minerals, in particular iron or copper ions, polysaccharides, and other components present in the extract are involved in the deodorization mechanism.

The mushroom contains a lot of polyhydric phenols. This is evidenced by the fact that the mushroom causes browning faster than other Hymenomycetes. In addition, it further comprises a large amount of proteins and free amino acids. Further, the content of iron and copper thereof are also high. Therefore, it is assumed that the mushroom is particularly effective for deodorizing mercaptans.

It has widely been known that many polysaccharides having specific physiological activity are generally present in Hymenomycetes in a small amount. Likewise, it is believed that unknown components included in the mushroom exerts influence on the metabolism of alcohol in liver or on the enteric bacteria to thus prevent giving out of bad smell.

The liquid extracted from the fruit-body of champignon mushroom or the extract per se may be used as the deodorizer of the present invention. Alternatively, they can further be processed and seasoned or flavored to add them to various drinks, solutions or aerosol preparations; or the extract is lyophilized to form powder of the effective components. Thus, the powder can be incorporated into a variety of basic materials to obtain various foods such as chewing gums, candy and sprinkled foods, feeds such as foods for pets and buccal compositions such as tooth paste and an agent for washing and preventing giving out of bad smell from false teeth. In addition, it can be taken in combination with other drugs such as a medicine for the stomach and bowels in the form of a liquid, powder or tablets, or further it may be incorporated into these drugs.

Dimethyl ether (DME) or the like are preferred as propellants for aerosol compositions.

The amount of the deodorizer of the present invention to be incorporated into a variety of basic materials is not restricted to a specific level, but it in general ranges from 0.01 to 5% by weight (solid content), preferably 0.1 to 3% by weight (solid content) based on the weight of the material.

The present invention will hereunder be explained in more detail with reference to the following non-limitative working Examples and Preparation Examples.

PREPARATION EXAMPLE 1

Roots of fresh champignon mushroom (1 kg; White species; closed cap) were cut off, followed by roughly washing with water, freezing, slicing into pieces having a width of about 3 mm and extracting with 3 kg of a 0.5% aqueous citric acid solution (pH 3.2) at 80° C. for 2 hours. The solution was filtered through a microfilter to obtain 2.5 kg of a pale yellow extract (1) (solid content: 2.0%).

PREPARATION EXAMPLE 2

Roots of fresh champignon mushroom (1 kg; White species; closed cap) were cut off, followed by lightly washing with water, freezing, slicing into pieces having a width of about 3 mm and extracting with 3 kg of a 30% ethanol/water mixed solution at 60° C. for 6 hours. The solution was filtered to obtain 2.5 kg of a pale yellow extract (2) (solid content: 2.0%).

PREPARATION EXAMPLE 3

Ethanol was distilled off under reduced pressure from the extract (2) (1 kg) and the extract was further condensed to obtain 200 g of residue. The residual solution was lyophilized to recover 20 g of pale yellow powder (3) of the extracted substances.

PREPARATION EXAMPLE 4

Roots of fresh champignon mushroom (1 kg; White species; closed cap) were cut off, followed by lightly washing with a 0.5% malic acid solution, slicing into pieces having a width of about 3 mm and introducing them into 3 kg of an aqueous solution (pH 3.2) containing 0.5% malic acid and 5% fruit sugar to perform extraction at 80° C. for 2 hours. The solution was filtered through a microfilter to obtain 2.7 kg of a pale yellow extract (4) (solid content: 7.0%).

PREPARATION EXAMPLE 5

Roots of fresh champignon mushroom (1 kg; White species; closed cap) were cut off, followed by lightly washing with water, freezing, slicing into pieces having a width of about 3 mm and adding 1 g of crude cellulase enzyme of mold fungi (available from NAGASE CO., LTD.) and 1 g of crude β-amylase enzyme (available from NAGASE CO., LTD.), immersing in a 0.2% aqueous solution of citric acid (pH 3.5) to carry out a reaction at 30° C. for 6 hours, thereafter heating the solution at 80° C. for 30 minutes, cooling the solution and filtering the solution with a microfilter to obtain 2.5 kg of a pale yellow extract (5) (solid content: 1.6%). The extract (5) was condensed under reduced pressure to obtain 200 g of a residual solution and then it was lyophilized to recover about 40 g of pale yellow powder (6).

PREPARATION EXAMPLE 6

Roots of mature champignon mushroom which had just formed its spore (1 kg; White species) were cut off, the surface thereof was lightly washed with water and the mushroom was immersed in 1 kg of water (pH 6.0) maintained at 20° C. for 2 hours to perform extraction. The dark purple extract was filtered through a screen of 300 mesh, the filtrate was stored at 5° C. for 24 hours and thereafter the filtrate was filtered through a microfilter to obtain 0.7 kg of a pale purple extract (7). 0.5 kg of the pale purple extract (7) (solid content: 2.0%) was lyophilized to thus obtain 10 g of pale purple powder (8) of the extract.

EXAMPLES 1 TO 6

Utilizing the extract (1) or (4) of the present invention, there were prepared preparations for drinking (100 ml per bottle) as listed in the following Table I.

TABLE I

| Component | Amount (grs. per 100 ml) | | |
|---|---|---|---|
| | Example 1 | Example 2 | Control 1 |
| Grape sugar | 6.0 | 6.0 | 6.0 |
| Fruit sugar | 6.0 | — | 6.0 |
| Citric acid | 0.2 | — | 0.2 |
| Ascorbic acid | 0.1 | 0.1 | 0.1 |
| Extract (1) of the invention | 30 | — | — |
| Extract (4) of the invention | — | 30 | — |
| Purified water | 57.6 | 63.8 | 87.6 |
| Flavor | 0.1 | 0.1 | 0.1 |

Using the powder (3) and (8) of the extracts of the present invention, chewing gum (3 g per sheet) as listed in the following Table II was prepared.

TABLE II

| Component | Amount (grs. per 100 ml) | | |
|---|---|---|---|
| | Example 3 | Example 4 | Control 2 |
| Palatinit | 62.7 | 63.7 | 64.7 |
| Gum base | 25 | 25 | 25 |
| 70% Soribitol solution | 5.3 | 5.3 | 5.3 |
| Glycerin | 5.0 | 5.0 | 5.0 |
| Powder (3) of the extract | 2.0 | — | — |
| Powder (8) of the extract | — | 1.0 | — |

Using the powder (6) of the extract of the present invention, pieces of candy (3 g) as listed in the following Table III were prepared.

TABLE III

| Component | Amount (grs. per 100 g) | |
|---|---|---|
| | Example 5 | Control 3 |
| Granular sugar | 60 | 62 |
| Sugaralcohol | 20 | 20 |
| Sour agent | 0.5 | 0.5 |
| Powder (6) of the extract of the present invention | 2.0 | — |
| Perfume derived from fruit | q.s. | q.s. |
| Coloring agent | q.s. | q.s. |
| Purified water | 17.5 | 17.5 |

Using the powder (3) of the extract of the present invention, water-soluble tablets as listed in the following Table IV were prepared (5 g per tablet).

TABLE IV

| Component | Amount (grs. per 100 g) | |
|---|---|---|
| | Example 6 | Control 4 |
| Granular sugar | 10 | 11 |
| Powder (3) of the extract | 1.0 | — |
| Sodium bicarbonate | 65 | 65 |
| Citric acid | 24 | 24 |

Foul breath removing effect of the products obtained in Examples 1 to 6 was examined by organoleptic examination using 8 panelists.

As an artificial foul breath solution, there was prepared a mercaptan solution comprising 10 mg of methyl mercaptan in 1000 ml of purified water, the panelists' mouths were rinsed with 20 ml of the artificial foul breath solution for one minute, each of the products obtained in Examples 1 to 6 was administered to 4 panelists in a rate of one product per day, while each of the control substances was internally administered to 4 other panelists in the same rate, and breath analysis was performed 10 minutes after the administration by two specialists. On the other hand, regarding the smell of garlic, 4 dumplings stuffed with minced pork (containing 0.5 g each of garlic) were fed to each panelist, then the product of the present invention was administered to each panelist 5 minutes after eating the dumplings and the same breath analysis was carried out 10 minutes after the administration.

Regarding the smell of fish, a roast fish was fed to each panelist, the product of the present invention was administered to each panelist 5 minutes after eating the roast fish and the same breath analysis was carried out 10 minutes after the administration. With regard to the smell of tobacco, the product of the present invention was administered to each panelist, who had smoked three pieces of tobacco (Mild Seven) up to 2 cm from their bases for 5 minutes, 5 minutes after the smoking and the same breath analysis was carried out 10 minutes after the administration.

The dose of each product or control substance is as shown in the following Table V.

TABLE V

| Example No. | Dosage Form | Dose(g) | Route for Medication |
|---|---|---|---|
| 1, 2 | drink | 100 | Drinking as such |
| 3, 4 | gum | 3 | chewing for 3 min. |
| 5 | candy | 3 | chewing the candy up to its complete dissolution |

TABLE V-continued

| Example No. | Dosage Form | Dose(g) | Route for Medication |
|---|---|---|---|
| 6 | tablet | 5 | drinking after dissolving it in a glass of water. |

The results of these organoleptic examinations on the deodorizing effect were evaluated on the basis of the following 5-stage evaluation standard. The results are the averages of 4 panelists.

TABLE VI

| | |
|---|---|
| 0 | severe smell (specific to each examination) |
| 1 | strong smell |
| 2 | smell immediately detected |
| 3 | smell detectable with difficulty |
| 4 | smell almost undetectable |

The results observed in each organoleptic examination are summarized in the following Table VII.

TABLE VII

| | Present Invention | | | | | Control | | | | |
|---|---|---|---|---|---|---|---|---|---|---|
| | panelist | | | | | panelist | | | | |
| Product | A | B | C | D | average | E | F | G | H | average |
| (1) Smell of mercaptan | | | | | | | | | | |
| Ex. 1 | 3 | 3 | 4 | 3 | 3.25 | 1 | 0 | 1 | 0 | 0.50 |
| 2 | 3 | 4 | 3 | 3 | 3.25 | 0 | 1 | 1 | 1 | 0.75 |
| 3 | 3 | 3 | 4 | 3 | 3.25 | 1 | 1 | 1 | 1 | 1.00 |
| 4 | 4 | 3 | 3 | 3 | 3.25 | 1 | 1 | 1 | 0 | 0.75 |
| 5 | 3 | 3 | 4 | 4 | 3.50 | 0 | 1 | 0 | 0 | 0.25 |
| 6 | 3 | 4 | 3 | 3 | 3.25 | 1 | 0 | 0 | 1 | 0.50 |
| (2) Smell of garlic | | | | | | | | | | |
| Ex. 1 | 3 | 3 | 3 | 3 | 3.00 | 0 | 0 | 0 | 1 | 0.25 |
| 2 | 3 | 3 | 2 | 3 | 2.75 | 1 | 0 | 0 | 1 | 0.50 |
| 3 | 3 | 2 | 3 | 3 | 2.75 | 1 | 1 | 1 | 0 | 0.75 |
| 4 | 2 | 3 | 2 | 3 | 2.50 | 0 | 1 | 0 | 1 | 0.50 |
| 5 | 3 | 3 | 2 | 2 | 2.50 | 1 | 0 | 0 | 0 | 0.25 |
| 6 | 2 | 3 | 3 | 3 | 2.75 | 1 | 1 | 0 | 0 | 0.50 |
| (3) Smell of fish | | | | | | | | | | |
| Ex. 1 | 4 | 3 | 4 | 4 | 3.75 | 1 | 2 | 1 | 1 | 1.25 |
| 2 | 3 | 4 | 4 | 4 | 3.75 | 2 | 2 | 1 | 1 | 1.50 |
| 3 | 3 | 3 | 3 | 4 | 3.25 | 1 | 1 | 1 | 2 | 1.25 |
| 4 | 3 | 3 | 4 | 4 | 3.50 | 1 | 1 | 2 | 2 | 1.50 |
| 5 | 3 | 3 | 4 | 3 | 3.25 | 1 | 1 | 1 | 2 | 1.25 |
| 6 | 3 | 4 | 3 | 4 | 3.50 | 2 | 1 | 2 | 2 | 1.75 |
| (4) Smell of tobacco | | | | | | | | | | |
| Ex. 1 | 4 | 3 | 3 | 3 | 3.25 | 0 | 1 | 0 | 0 | 0.25 |
| 2 | 3 | 3 | 4 | 3 | 3.25 | 0 | 0 | 1 | 0 | 0.25 |
| 3 | 4 | 3 | 4 | 3 | 3.50 | 1 | 1 | 1 | 0 | 0.75 |
| 4 | 4 | 4 | 3 | 4 | 3.75 | 1 | 1 | 1 | 1 | 1.00 |
| 5 | 3 | 3 | 4 | 3 | 3.25 | 0 | 0 | 0 | 0 | 0.00 |

As is clear from the results listed in Table VII, all of the deodorizers of the present invention show excellent effect of removing smell.

Panelists were divided into groups each comprising 4 persons as in the foregoing foul breath test, a bottle of beer (633 ml) was fed to each panelist before going to bed and 10 minutes after drinking beer, each of the products obtained in Examples 1 to 6 or each of the control substances 1 to 4 was administered to each panelist. The urine initially discharged from each panelist in the next morning was collected and its smell was examined and evaluated. The smell thereof was evaluated according to the following 5-stage evaluation standard shown in Table VIII.

TABLE VIII

| | |
|---|---|
| 0: | severe, specific but slightly sweet smell (smell of aldehyde) |
| 1: | strong smell |
| 2: | smell immediately detected |
| 3: | smell detectable with difficulty |
| 4: | smell almost undetectable |

The results obtained are summarized in the following Table IX.

TABLE IX

Smell of the Urine Discharged After Drinking Beer.

| | Present Invention | | | | | Control | | | | |
|---|---|---|---|---|---|---|---|---|---|---|
| | panelist | | | | | panelist | | | | |
| Product | A | B | C | D | average | E | F | G | H | average |
| Ex. 1 | 3 | 4 | 3 | 3 | 3.25 | 1 | 2 | 1 | 1 | 1.25 |
| 2 | 4 | 3 | 3 | 3 | 3.25 | 1 | 2 | 1 | 0 | 1.00 |
| 3 | 3 | 3 | 3 | 2 | 2.75 | 1 | 1 | 2 | 1 | 1.25 |
| 4 | 3 | 2 | 3 | 2 | 2.50 | 2 | 1 | 1 | 1 | 1.25 |
| 5 | 2 | 3 | 3 | 2 | 2.50 | 1 | 2 | 2 | 0 | 1.25 |
| 6 | 3 | 4 | 3 | 3 | 3.25 | 1 | 1 | 1 | 1 | 1.00 |

As seen from the results listed in Table IX, the specific smell observed after drinking alcoholic drinks can be reduced by the administration of the products of the present invention.

EXAMPLE 7

Using the powder (8) of the extract of the present invention, there were prepared foods for pets as shown in the following Table X.

TABLE X

| | Amount (grs. per 100 g) | |
|---|---|---|
| Component | Example 7 | Control 5 |
| Minced pork | 90 | 90 |
| Thickening agent | 1.0 | 1.0 |
| Stabilizer | 0.5 | 0.5 |
| Seasoning | 3.0 | 3.0 |
| Powder (8) of the extract | 1.0 | — |
| Water | 4.5 | 5.5 |

150 g each of the control substance 5 was fed to two dogs A and B twice a day for 3 days and then 150 g each of the food for pet obtained in Example 7 was likewise fed to them twice a day for the subsequent 3 days. The feces thereof were collected and the smell thereof was examined to estimate the difference in the smell.

The results observed are listed in Table XI below. The smell of the feces was estimated and expressed by five steps using symbol (+). The greater the number of the symbols (+), the stronger the bad smell.

TABLE XI

| Collecting time | Deodorizer | Smell of the Feces | |
| --- | --- | --- | --- |
| | | dog A | dog B |
| 1st day | control | +++ | +++ |
| 2nd day | control | ++++ | +++++ |
| 3rd day | control | ++++ | +++++ |
| 4th day | Example 7 | +++ | +++ |
| 5th day | Example 7 | ++ | ++ |
| 6th day | Example 7 | + | ++ |

As seen from the results listed in Table XI, the disgusting smell of the feces could be eliminated by feeding the food for pet according to the present invention to animals, several days after the initiation of its feeding.

EXAMPLES 8 AND 9

Using the extracts (1) and (2) of the present invention, there were prepared aerosols having the following composition as listed in Table XII given below.

TABLE XII

| Component | Amount (ml/100 ml) | | |
| --- | --- | --- | --- |
| | Ex. 8 | Ex. 9 | Control |
| Extract (1) of the present invention | 20.0 | — | — |
| Extract (2) of the present invention | — | 20.0 | — |
| Ethanol | 15.0 | 9.0 | 15.0 |
| Purified water | 15.0 | 21.0 | 35.0 |
| DME | 50.0 | 50.0 | 50.0 |

A 4 l airtight sealable container was previously filled with the vapor of a constant volume of each of four kinds of standard formulations which give out bad smell and have the following composition, followed by spraying the aerosol obtained in Example 8 or 9 or a control aerosol in the container through a nozzle for 2 seconds, sealing the container and then detecting the residual concentration of the gas giving out bad smell with time by a detecting tube (available from KITAGAWA GAS DETECTING TUBE MANUFACTURING CO., LTD.). The results thus obtained are summarized in the following Table XIII.

TABLE XIII

| Gas | Aerosol | Concentration (ppm) | | | | |
| --- | --- | --- | --- | --- | --- | --- |
| | | before spraying | time elapsed after spraying (min) | | | |
| | | | 5 | 10 | 30 | 60 |
| Ammonia | Ex. 8 | 1100 | 5 | 6 | 0 | 0 |
| | Ex. 9 | 1000 | 3 | 4 | 2 | 0 |
| | control | 980 | 350 | 340 | 320 | 300 |
| Trimethyl-amine | Ex. 8 | 300 | 10 | 10 | 7 | 0 |
| | Ex. 9 | 310 | 13 | 12 | 8 | 1 |
| | control | 295 | 115 | 105 | 97 | 95 |

TABLE XIII-continued

| Gas | Aerosol | Concentration (ppm) | | | | |
| --- | --- | --- | --- | --- | --- | --- |
| | | before spraying | time elapsed after spraying (min) | | | |
| | | | 5 | 10 | 30 | 60 |
| Formaldehyde | Ex. 8 | 30 | 5 | 4 | 2 | 0 |
| | Ex. 9 | 32 | 6 | 5 | 3 | 1 |
| | control | 31 | 21 | 20 | 18 | 17 |
| Methyl mercaptan | Ex. 8 | 10 | 4 | 4 | 2 | 1 |
| | Ex. 9 | 10 | 4 | 3 | 2 | 1 |
| | control | 10 | 7 | 7 | 6 | 6 |

As seen from the results listed in Table XIII, the products obtained in Examples 8 and 9 show excellent deodorizing effect compared with the control.

In Examples 8 and 9, hydrophilic solvents other than ethanol such as isopropyl alcohol or acetone may be used, but ethanol is preferred because of its non-toxicity and its smell.

As the propellants, LPG and Freon (trade name) may be used in addition to DME, but DME is preferred from the viewpoint of its compatibility with water. Moreover, carbon dioxide gas or compressed air may also be employed as a propellant.

The deodorizers of the present invention are safe since they comprise extracts obtained from edible mushrooms and they are capable of oral intake. Therefore, they can suppress foul breath by drinking, chewing or licking the deodorizer of the invention. In addition, they can be absorbed in the body and exert influence on the alcohol metabolism to thus reduce the bad smell of the urine due to the generation of aldehydes or to reduce the smell of feces as evidenced by the experiments of the food for pet. Such specific effects have not been achieved by conventional deodorizers for environment.

Moreover, the deodorizer of the present invention is excellent in deodorizing substances which give out bad smell such as ammonia, trimethylamine, hydrogen sulfide, methyl mercaptan, acetaldehyde and formalin. Therefore, the products of the present invention can widely be applied as deodorizers for environment such as those for deodorizing kitchen waste, a lavatory, the interior of a room and the inside of a car, as well as a factory and a cattle shed.

What is claimed is:

1. A food containing a hydrophilic solvent extract of fruit-bodies of champignon mushroom (*Agaricus bisporus*) or powder of the extract in an amount of 0.01% to 50% by weight based on the total weight of the food.

2. A food produced by extracting champignon mushrooms (*Agaricus bisporus*) with a hydrophilic solvent at a temperature of 60° C. to 100° C. for 15 minutes to two hours to provide an extract or a powder, the extract or powder comprising 0.01 to 50% by weight of the total weight of the food.

* * * * *

UNITED STATES PATENT AND TRADEMARK OFFICE
CERTIFICATE OF CORRECTION

PATENT NO : 5,804,174
DATED : September 8, 1998
INVENTOR(S) : Sadami Ishibashi et al.

It is certified that error appears in the above-identified patent and that said Letters Patent is hereby corrected as shown below:

On the title page: Item [56]

References Cited, following "4,472,046", please delete "9/1984" and insert therefor --8/1988--.

Abstract, in line 7, please delete "1000° C." and insert therefor --100° C.--.

Signed and Sealed this

Seventeenth Day of August, 1999

Attest:

Attesting Officer

Q. TODD DICKINSON

Acting Commissioner of Patents and Trademarks